United States Patent [19]

Perten

[11] Patent Number: 4,953,401
[45] Date of Patent: Sep. 4, 1990

[54] METHOD FOR DETERMINING THE QUALITY OF GLUTEN IN WHEAT

[76] Inventor: Harald Perten, Sonder 14-17, CH-9042 Speicher, Switzerland

[21] Appl. No.: 391,523

[22] PCT Filed: Nov. 3, 1987

[86] PCT No.: PCT/SE87/00514
§ 371 Date: Jul. 3, 1989
§ 102(e) Date: Jul. 3, 1989

[87] PCT Pub. No.: WO89/04483
PCT Pub. Date: May 18, 1989

[51] Int. Cl.$^5$ ............................................. G01N 33/10
[52] U.S. Cl. ...................................... 73/169; 494/10; 530/374
[58] Field of Search ............... 73/169, 56, 866, 53, 73/61.4; 209/237; 494/10, 43; 530/374

[56] References Cited

U.S. PATENT DOCUMENTS

| 3,169,395 | 2/1965 | Enoch et al. | 73/169 |
| 3,651,768 | 3/1972 | Hyppölä426 | 331/ |
| 4,125,528 | 11/1978 | Lao et al. | 530/374 |

FOREIGN PATENT DOCUMENTS

| 2055025 | 11/1970 | Fed. Rep. of Germany | 73/169 |
| 0826230 | 4/1981 | U.S.S.R. | 73/169 |
| 0826231 | 4/1981 | U.S.S.R. | 73/169 |
| 36914 | 3/1933 | United Kingdom | 73/109 |

Primary Examiner—Allan N. Shoap
Assistant Examiner—Alvin Wirthlin
Attorney, Agent, or Firm—Fleit, Jacobson, Cohn, Price, Holman & Stern

[57] ABSTRACT

The quality of gluten in wheat is determined by centrifuging a gluten sample taken from a wheat dough against a sieve. Upon completion of the centrifugation process, it is determined how large a proportion of the sample has remained in the sieve, without penetrating therethrough. The magnitude of this proportion is used as a measurement of the gluten quality.

11 Claims, 2 Drawing Sheets

METHOD FOR DETERMINING THE QUALITY OF GLUTEN IN WHEAT

The present invention relates to a method for determining the quality of gluten in wheat, in which method a gluten sample taken from wheat dough is placed on a sieve in a centrifuge and centrifuged against the sieve.

When determining the quality of wheat flour, it is normal to establish the amount of protein and gluten contained therein. This can be achieved with the aid of relatively simple methods which can be quickly carried out. This analysis alone, however, is not sufficient to assess the baking properties of the flour with any degree of surety, since two flours which have mutually the same protein or gluten content may have totally different baking properties, due to the fact that they have mutually different gluten properties. There is a great need to be able to establish the gluten quality in wheat in a sample and reliable manner, this need being found particularly among wheat growers, millers and bakers.

When determining the gluten content of wheat flour, it is normal practice to prepare a wheat dough from a given quantity of wheat flour and to remove the starch from the dough, by treating the dough in a jet of water. This procedure results in a residual product of water-insoluble, wet gluten which contains 80–85% protein. A measurement of the gluten content of the flour can be obtained by weighing the gluten making up the residual product. Since the gluten content and the protein content are mutually proportional, there is also obtained in this case a measurement of the protein content of the flour.

It can be ascertained manually that the properties of the gluten obtained in this way may vary from flour to flour.

For example, the gluten can be dry, elastic inelastic, short, stretchable, slimy, tacky, etc. Manual characterization of the properties of the gluten is not considered to give a sufficiently reliable and clear result. There is, however, no internationally accepted method for determining gluten quality analytically.

Many different types of apparatus have been constructed for measuring the rheological, i.e. elastic, plastic and viscous properties of the gluten. One type of apparatus is based on the method of measuring the stretchability of the gluten when subjected to a given force over a given period of time. Another type of apparatus is based on the method of first subjecting the gluten to a given force over a given period of time and then measuring restoration of the gluten to its original state. Another type of apparatus is based on the method of placing a gluten sample between a plate and a cone, subjecting the sample to torsional forces, and measuring the relaxation properties of the sample. None of these apparatus, however, has found general use, due to the fact that the methods supplied therewith are too complicated and the apparatus too expensive.

In certain countries, e.g. Austria, the swelling-index method (German: Quellzahl) is used officially to determine the gluten quality and baking properties of wheat flour. This method is based on degrading the gluten in lactic acid and recording the degradation effect. The method is both complicated and highly time consuming (3–4 hours are required in order to carry the method into effect).

The object of the present invention is to enable the quality of gluten in wheat to be determined analytically in a simple and positive manner.

This object is achieved in accordance with the invention by determining the amount of gluten which penetrates the sieve under the influence of the centrifugal force generated, and using this penetrative amount as a measurement of the gluten quality. More particularly, subsequent to centrifuging the sample there is determined the ratio between the amount of gluten which has not passed through the sieve and the total amount of gluten present.

A particular advantage is afforded in this regard when the extent to which the gluten sample passes through a special sieve is determined in combination with the centrifugation process normally carried out to determine the gluten content of flour, e.g. with the aid of an apparatus Glutomatic manufactured by Falling Number AB in Sweden. The only additional working procedure that need be carried out in comparison with the known procedure is that of weighing the portion of the gluten sample located on one side or the other of the sieve.

Further features of the invention and advantages afforded thereby will be apparent from the following description and claims.

The invention will now be described in more detail with the aid of an exemplifying embodiment thereof illustrated in the accompanying drawings, in which FIG. 1 is a schematic view from above of test apparatus for carrying out the method according to the invention;

For the purpose of determining the quality of the gluten in wheat there is first prepared a dough from a given amount of wheat flour, and the dough is washed under a jet of water so that the water-insoluble part of the dough remains, this residual product consisting of wet gluten. The separation of the gluten can be achieved readily and simply with the aid, e.g. of an apparatus Glutomatic manufactured by Falling Number AB in Sweden.

This apparatus includes a centrifuge for removing excess water from the wet gluten. The normal practice hitherto has been to place the wet gluten against a sieve in the centrifuge and to subject the gluten to centrifugation, whereafter the gluten is collected and weighed in order to determine the gluten content of the flour. It has surprisingly been found in accordance with the invention, however, that this centrifugation can be utilized not only to determine the gluten content of the flour, but also to determine the quality of the gluten analytically.

Experiments have shown that there is a direct relationship between gluten quality and the ability of the gluten sample to pass through the sieve under the influence of centrifugal force. The extent to which the sample penetrates the sieve can be established easily, by weighing, for instance, the amount of gluten which does not pass through the sieve in addition to weighing the total amount of gluten in accordance with the earlier known procedure. Thus, it has been found that the method applied at present to determine the gluten content can be readily complemented in a manner which will also enable the quality of the gluten to be determined at an insignificant extra cost and with but a negligible amount of additional labor.

Figure 1:
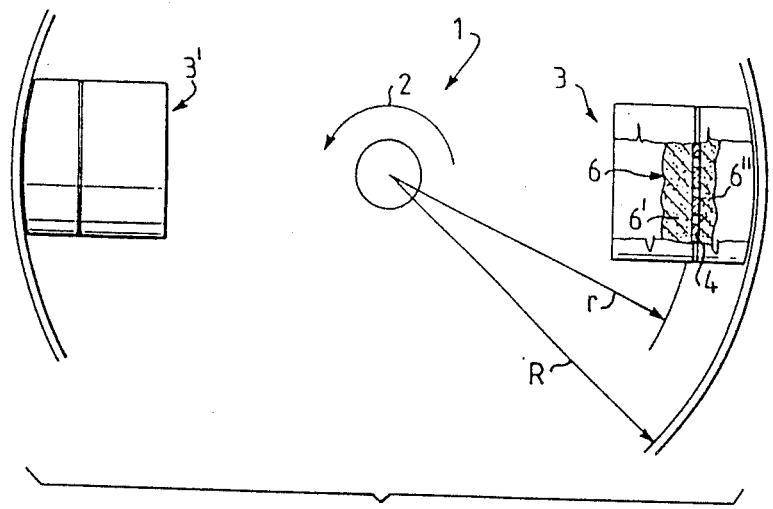
Figure 2:
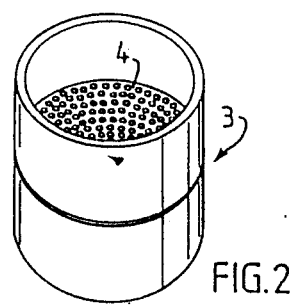
FIG. 2 is a perspective view of a sample container used in FIG. 1.
Figure 3:
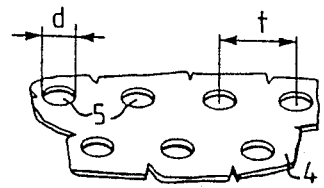
FIG. 3 illustrates a part of the sieve incorporated in the sample container.

FIG. 1 illustrates how, in accordance with the invention, a conventional centrifuge 1 of the kind used in the aforementioned apparatus Glutomatic is used to determine both the gluten content and the gluten quality at one and the same time, with the use of the wet gluten obtained when washing wheat dough in a conventional manner. The centrifuge 1 has a wall radius R of about 60 mm and a working speed n of about 6000 rpm and rotates in the direction indicated by the arrow 2. Arranged in the centrifuge 1 are two mutually identical, substantially tubular gluten sample containers 3 and 3'. Each container has a sieve-forming partition wall 4 which during the process of centrifugation is located at a distance r of about 49 mm from the centrifuge centre and is provided with a large number of holes 5 of diameter d which have a mutual spacing t—(see FIG. 3). Prior to centrifugation, a gluten sample 6 is placed on the side of the sieve 4 facing the centre of the centrifuge and during the centrifuging process part of the sample will be forced through the sieve 4, so that upon completion of the centrifugation process an inner sample part 6' will be located inwardly of the sieve and an outer sample part 6" will be located outwardly thereof. The proportional relationship between either one of the sample parts 6' and 6" and the whole of the sample 6 can be readily determined by weighing said sample part and said whole sample, and has been found to constitute a measurement of the quality of the gluten.

It will readily be understood that a given type of gluten will penetrate the sieve 4 to varying degrees, depending upon the magnitude of the centrifugal force generated (a function of the speed n and the centrifuging radius r), the length of time over which the sample is centrifuged, and the sieve construction. It has also been found that the waiting time prior to centrifugation plays a significant part in the extent to which the gluten penetrates the sieve. The extent to which the gluten penetrates the sieve increases with increasing centrifugal force and increasing centrifuging time, and also with increasing mesh size.

If, however, different sorts of flour are tested under the same conditions, i.e. at mutually the same centrifugal force and are centrifuged for mutually the same length of time with the aid of one and the same sieve and with the same waiting period to centrifugation, it is possible to graduate the quality of the gluten in the various flour sorts on the basis of the measured extend of penetration through the sieve.

The tests can be made more revealing or indicative within certain quality intervals, by changing the test conditions. For instance, by using a coarse sieve it is easier to measure differences in quality between such gluten samples that when using a fine sieve would show only small differences, due to the fact the samples find it difficult to pass through a fine sieve. This may be of particular interest in those areas of the quality scale in which the limit between bake-ability and non-bake ability for the flour concerned is located.

Table I below recites the test results obtained in the case of various fours, where the samples were centrifuged for 1 minute at a centrifuge speed n of 6000 rpm, and a distance r from the centrifuge centre of 49 mm. Two different sieves were used, the one with d=0.60 mm and t=0.40 mm, and the other with d=0.75 mm and t=0.50 mm. The waiting time prior to centrifugation was about one minute.

TABLE I

| Wheat flour | Gluten content % | $Q_o$ | $Q_{30}$ | Gluten index d = 0.6 mm | d = 0.75 mm |
|---|---|---|---|---|---|
| nr 1 | 34.5 | 28 | 24 | 98.7 | 98.2 |
| nr 2 | 31.8 | 26 | 22 | 95.4 | 87.6 |
| nr 3 | 35.9 | 23 | 14 | 91.4 | 81.5 |
| nr 4 | 31.1 | 20 | 13 | 93.1 | 88.6 |
| nr 5 | 39.8 | 18 | 11 | 74.6 | 64.0 |
| nr 6 | 38.7 | 15 | 8 | 67.7 | 51.6 |
| nr 7 | 36.0 | 10 | 6 | 32.0 | 14.5 |
| nr 8 | 32.6 | 5 | 1 | 8.5 | — |

The term gluten index used in Table I relates to the percentage of the sample that remains on the sieve upon completion of the centrifugation process, and thus constitutes a measurement of the ability of the sample to penetrate the sieve. Thus, a high gluten index indicates a high sieve retention property of the gluten, whereas a low gluten indicates a low sieve retention property of the gluten. It will be seen from the Table that the gluten index decreases with decreasing "Quellzahl" $Q_o$ or $Q_{30}$ (wherein $Q_o$ is the initial swelling index, and $Q_{30}$ is the swelling index after 30 minutes and that there is thus a relationship between the quality term "Quellzahl" and gluten index. It will also be seen that the gluten index for a given wheat flour will decrease with increasing hole sizes in the sieve.

Figure 4:
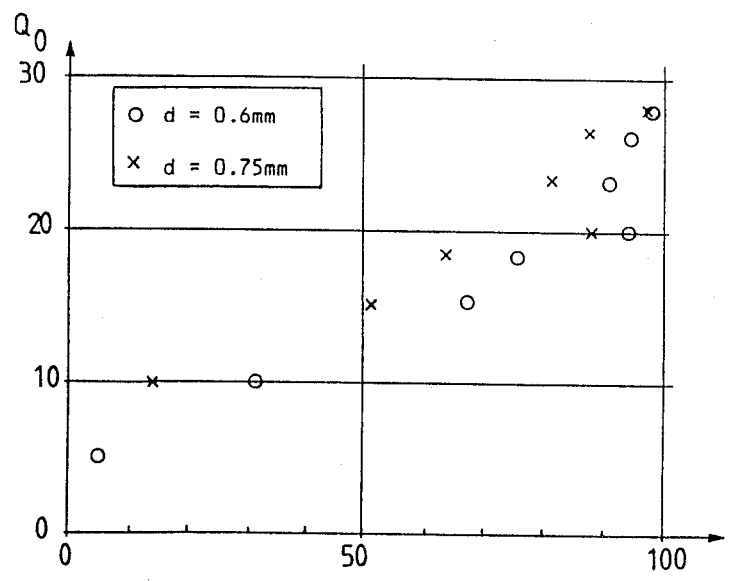
FIG. 4 is a diagram which shows the relationship between Quellzahl $Q_o$ and gluten index for various gluten samples.

FIG. 4 illustrates graphically, on the basis of Table I, the relationship between gluten index and "Quellzahl" $Q_o$. It will be seen from this graphic illustration that there is a clear relationship between gluten index and $Q_o$. Thus, it is possible to obtain a measurement of the gluten quality on the basis of the gluten index.

In some countries the law requires the gluten to have a $Q_o$ off at least 14 in order to have acceptable baking properties. In FIG. 4 this corresponds to a gluten index of at least about 60 with a sieve having a hole diameter of d=0.6 mm. Different test series have shown that the reproducibility is good.

A sample container 3 of the illustrated kind has been found particularly suitable for manipulating the gluten sample, which is prevented from spreading in the circumferential direction of the centrifuge by the walls surrounding the sieve. This greatly facilitates collection and weighing of the sample parts. The configuration of the sample container and its positioning in the centrifuge can, of course, be varied in many different ways. For example, the number of sample containers used may be varied in accordance with requirements, while taking into consideration the problems of balance in the centrifuge.

For the purpose of determining the influence of the waiting time of the gluten sample in the gluten index, a sample can be centrifuged several times. For example, the sample can be centrifuged after a waiting time of one minute and then centrifuged again after a further waiting time of e.g. 30 minutes. By centrifuging the whole sample each time, it is not necessary to divide the sample down into smaller portions, although the sample can be divided-up, of course, if so desired.

Those experiments carried out hitherto have shown that the gluten quality of wheat flour can be determined in a very reliable and very simple manner with the aid of standardized testing procedures.

I claim:

1. A method of determining the quality of gluten in wheat, in which method a gluten sample taken from a wheat dough is placed on a sieve in a centrifuge and centrifuged against the sieve, characterized by determining the extent to which the gluten sample penetrates the sieve under the influence of the centrifugal force generated and taking this extent of penetration as a measurement of the gluten quality.

2. A method according to claim 1, characterized by determining the ratio between the amount of gluten that has not penetrated through the sieve and the total amount of gluten, upon completion of the centrifugation.

3. A method according to claim 1, characterized by performing the centrifugation at a pre-determined centrifugal force.

4. A method according to claim 3, characterized by using a centrifugal speed of about 6000 rpm, and by locating the sample at a maximum distance from the centre of the centrifuge of about 60 mm.

5. A method according to claim 4, characterized by continuing the centrifugation over a pre-determined length of time.

6. A method according to claim 5, characterized by continuing the centrifugation for about one minute.

7. A method according to claim 1, characterized by using a sieve of pre-determined properties.

8. A method according to claim 7, characterized in that the sieve has the form of a perforated plate in which the hole diameter is about 0.6 mm and the hole spacing is about 1.40 mm.

9. A method according to claim 8, characterized by placing the gluten sample on the sieve which is provided with circumferential walls on both sides thereof.

10. A method according to claim 9, characterized by commencing the centrifugation subsequent to the lapse of a pre-determined length of time from the time of obtaining the gluten sample, suitably a time lapse of one minute.

11. A method according to claim 10, characterized by centrifuging the gluten sample for at least a second time, suitably subsequent to a time lapse of 30 minutes from the time of completing the first centrifugation.

* * * * *